United States Patent [19]
Brocia

[11] Patent Number: 5,459,567
[45] Date of Patent: Oct. 17, 1995

[54] METHOD FOR DETERMINING THE DEGREE OF SPECTRAL INTERFERENCE IN AN ASSAY HAVING A TEST SAMPLE

[76] Inventor: Robert W. Brocia, 15 Moore Rd., Bronxville, N.Y. 10708

[21] Appl. No.: 198,995

[22] Filed: Feb. 18, 1994

[51] Int. Cl.[6] ..................................................... G01N 21/64
[52] U.S. Cl. ....................... 356/318; 356/417; 250/458.1; 250/459.1
[58] Field of Search ..................................... 356/317, 318, 356/417, 73; 250/458.1, 459.1, 461.1

[56] References Cited

U.S. PATENT DOCUMENTS

| | | | |
|---|---|---|---|
| 4,745,285 | 5/1988 | Recktenwald et al. | 356/318 |
| 4,821,080 | 4/1989 | Hayashi | 356/318 |
| 5,216,483 | 6/1993 | Berthold et al. | 356/318 |
| 5,400,137 | 3/1995 | Winslow et al. | 356/318 |

OTHER PUBLICATIONS

Charles L. Bisgaier, et al., "Use of Fluorescent Cholesteryl Ester Microemulsions in Cholesteryl Ester transfer Protein Assays", *Journal of Lipid Research*, vol. 34 (1993), pp. 1625–1634.
A. V. Nichols, et al., "Effect of Very Low–Density Lipoproteins on Lipid Transfer in Incubated Serum", *Journal of Lipid Research*, vol. 6 (1965), pp. 206–210.
N. M. Pattnaik, et al., "Cholesteryl Ester Exchange Protein in Human Plasma Isolation and Characterization", *Biochimica et Biophysica Acta*, vol. 530 (1978), pp. 428–438.
N. Dousset, et al., "Fluorescent Determination of Cholesteryl Ester Transfer Protein (CETP) Activity in Plasma", *Clinical Chemistry*, vol. 38, No. 2 (1982), p. 306.
T. G. Milner, et al., "Enhancement of the Human Plasma Lipid Transfer Protein Reaction by Apolipoproteins", *Biochimica et Biophysica Acta*, vol. 1082 (1991), pp. 71–78.
J. R. Wetterau, et al., "Protein Disulfide Isomerase Is a Component of the Microsomal Triglyceride Transfer Protein Complex", *The Journal of Biological Chemistry*, vol. 265, No 17 (Jun. 15, 1990), pp. 9800–9807.

*Primary Examiner*—F. L. Evans
*Attorney, Agent, or Firm*—Lackenbach Siegel Marzullo Aronson & Greenspan

[57] ABSTRACT

A method to determine the degree of spectral interference in an assay containing a test sample in which a graph plot of efficiency versus ratio of a fluorescence label is a known standard. The assay is placed in a fluorimeter and excited with light energy at the excitation wavelength of the fluorescence label. The entire emission spectrum is examined and an actual fluorescence emission intensity value is obtained from the assay which is representative of the activity of the test sample.

4 Claims, 17 Drawing Sheets

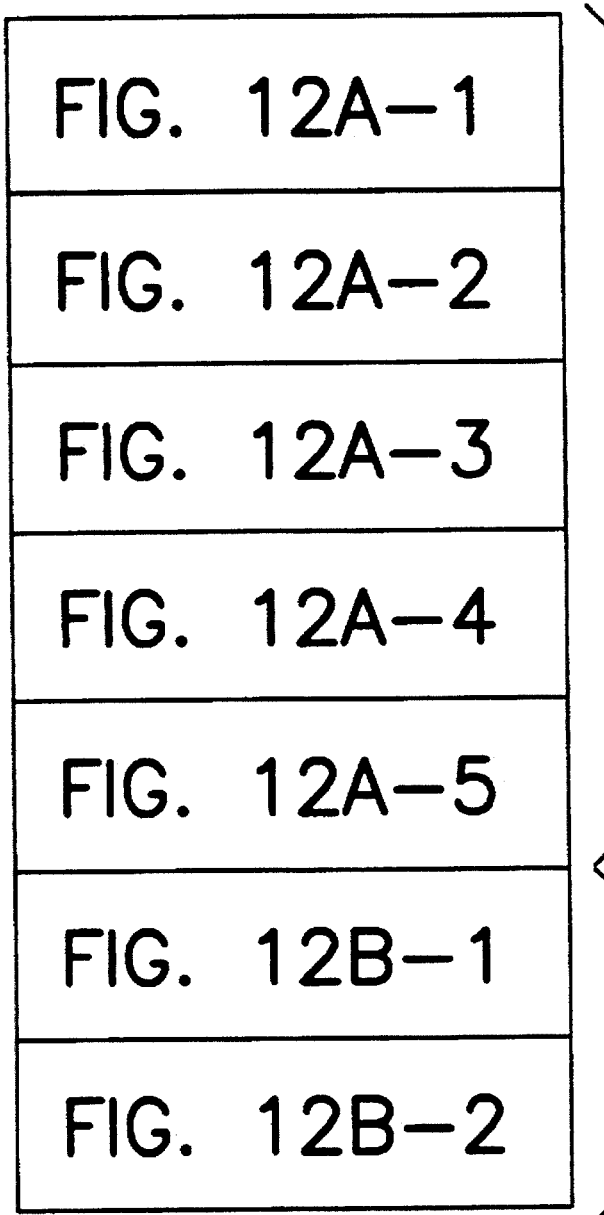

TECHNIQUE: PE FL
SUBTECHNIQUE: SUBTECH
TYPE: SPECTRUM
SAMPLE ID: 0QDM3001.TMP
DATA TYPE: BINARY
SOFTWARE ID: FLDM(v2.50)
ANALYST:
CREATED: 01:15:59,91/06/25
LAST MODIFIED: 01:15:59,91/06/25

DATA SET 1

| X(nm) | Y(INT) |
|---|---|
| 500 | 41.067 |
| 500.5 | 41.435 |
| 501 | 41.934 |
| 501.5 | 42.503 |
| 502 | 43.055 |
| 502.5 | 43.527 |
| 503 | 43.923 |
| 503.5 | 44.293 |
| 504 | 44.683 |
| 504.5 | 45.086 |
| 505 | 45.456 |
| 505.5 | 45.758 |
| 506 | 46.017 |
| 506.5 | 46.285 |
| 507 | 46.578 |
| 507.5 | 46.863 |
| 508 | 47.11 |

2

TECHNIQUE: PE FL
SUBTECHNIQUE: SUBTECH
TYPE: SPECTRUM
SAMPLE ID: 106Q001.TM
DATA TYPE: BINARY
SOFTWARE ID: FLDM(v2.50)
ANALYST:
CREATED: 01:23:49,91/06/25
LAST MODIFIED: 01:23:49,91/06/25

DATA SET 1

| X(nm) | Y(INT) |
|---|---|
| 500 | 32.944 |
| 500.5 | 33.383 |
| 501 | 33.848 |
| 501.5 | 34.275 |
| 502 | 34.638 |
| 502.5 | 34.938 |
| 503 | 35.196 |
| 503.5 | 35.453 |
| 504 | 35.746 |
| 504.5 | 36.074 |
| 505 | 36.394 |
| 505.5 | 36.673 |
| 506 | 36.927 |
| 506.5 | 37.202 |
| 507 | 37.508 |
| 507.5 | 37.805 |
| 508 | 38.058 |

3

TECHNIQUE: PE FL
SUBTECHNIQUE: SUBTECH
TYPE: SPECTRUM
SAMPLE ID: 106Q001.TMP
DATA TYPE: BINARY
SOFTWARE ID: FLDM(v2.50)
ANALYST:
CREATED: 01:30:50,91/06/25
LAST MODIFIED: 01:30:50,91/06/25

DATA SET 1

| X(nm) | Y(INT) |
|---|---|
| 500 | 21.65 |
| 500.5 | 21.928 |
| 501 | 22.206 |
| 501.5 | 22.466 |
| 502 | 22.73 |
| 502.5 | 23.014 |
| 503 | 23.303 |
| 503.5 | 23.56 |
| 504 | 23.764 |
| 504.5 | 23.929 |
| 505 | 24.091 |
| 505.5 | 24.272 |
| 506 | 24.459 |
| 506.5 | 24.618 |
| 507 | 24.716 |
| 507.5 | 24.75 |
| 508 | 24.751 |

FIG. 12A-2

| | | | | | |
|---|---|---|---|---|---|
| 508.5 | 47.345 | 508.5 | 38.268 | 508.5 | 24.783 |
| 509 | 47.604 | 509 | 38.46 | 509 | 24.895 |
| 509.5 | 47.875 | 509.5 | 38.644 | 509.5 | 25.076 |
| 510 | 48.088 | 510 | 38.802 | 510 | 25.261 |
| 510.5 | 48.196 | 510.5 | 38.903 | 510.5 | 25.389 |
| 511 | 48.241 | 511 | 38.946 | 511 | 25.444 |
| 511.5 | 48.299 | 511.5 | 38.958 | 511.5 | 25.452 |
| 512 | 48.388 | 512 | 38.965 | 512 | 25.446 |
| 512.5 | 48.46 | 512.5 | 38.954 | 512.5 | 25.446 |
| 513 | 48.475 | 513 | 38.901 | 513 | 25.469 |
| 513.5 | 48.443 | 513.5 | 38.828 | 513.5 | 25.533 |
| 514 | 48.389 | 514 | 38.793 | 514 | 25.641 |
| 514.5 | 48.322 | 514.5 | 38.841 | 514.5 | 25.763 |
| 515 | 48.244 | 515 | 38.958 | 515 | 25.852 |
| 515.5 | 48.171 | 515.5 | 39.078 | 515.5 | 25.873 |
| 516 | 48.115 | 516 | 39.141 | 516 | 25.812 |
| 516.5 | 48.079 | 516.5 | 39.125 | 516.5 | 25.684 |
| 517 | 48.058 | 517 | 39.058 | 517 | 25.538 |
| 517.5 | 48.054 | 517.5 | 38.998 | 517.5 | 25.442 |
| 518 | 48.061 | 518 | 38.985 | 518 | 25.431 |
| 518.5 | 48.057 | 518.5 | 39.004 | 518.5 | 25.476 |
| 519 | 48.018 | 519 | 39.002 | 519 | 25.514 |
| 519.5 | 47.95 | 519.5 | 38.939 | 519.5 | 25.517 |
| 520 | 47.876 | 520 | 38.814 | 520 | 25.493 |
| 520.5 | 47.799 | 520.5 | 38.654 | 520.5 | 25.452 |
| 521 | 47.696 | 521 | 38.501 | 521 | 25.391 |
| 521.5 | 47.551 | 521.5 | 38.383 | 521.5 | 25.323 |
| 522 | 47.38 | 522 | 38.289 | 522 | 25.276 |
| 522.5 | 47.211 | 522.5 | 38.171 | 522.5 | 25.265 |
| 523 | 47.074 | 523 | 38.001 | 523 | 25.259 |
| 523.5 | 46.971 | 523.5 | 37.791 | 523.5 | 25.211 |
| 524 | 46.878 | 524 | 37.592 | 524 | 25.11 |

| | | | | | |
|---|---|---|---|---|---|
| 524.5 | 46.766 | 524.5 | 37.444 | 524.5 | 24.99 |
| 525 | 46.643 | 525 | 37.352 | 525 | 24.895 |
| 525.5 | 46.526 | 525.5 | 37.278 | 525.5 | 24.846 |
| 526 | 46.395 | 526 | 37.181 | 526 | 24.823 |
| 526.5 | 46.209 | 526.5 | 37.054 | 526.5 | 24.774 |
| 527 | 45.971 | 527 | 36.917 | 527 | 24.651 |
| 527.5 | 45.718 | 527.5 | 36.787 | 527.5 | 24.458 |
| 528 | 45.463 | 528 | 36.662 | 528 | 24.255 |
| 528.5 | 45.188 | 528.5 | 36.518 | 528.5 | 24.115 |
| 529 | 44.888 | 529 | 36.329 | 529 | 24.056 |
| 529.5 | 44.578 | 529.5 | 36.089 | 529.5 | 24.027 |
| 530 | 44.248 | 530 | 35.818 | 530 | 23.954 |
| 530.5 | 43.854 | 530.5 | 35.544 | 530.5 | 23.791 |
| 531 | 43.387 | 531 | 35.276 | 531 | 23.536 |
| 531.5 | 42.902 | 531.5 | 35.011 | 531.5 | 23.228 |
| 532 | 42.471 | 532 | 34.736 | 532 | 22.924 |
| 532.5 | 42.118 | 532.5 | 34.443 | 532.5 | 22.674 |
| 533 | 41.817 | 533 | 34.138 | 533 | 22.491 |
| 533.5 | 41.534 | 533.5 | 33.837 | 533.5 | 22.352 |
| 534 | 41.246 | 534 | 33.548 | 534 | 22.217 |
| 534.5 | 40.818 | 534.5 | 33.254 | 534.5 | 22.044 |
| 535 | 40.505 | 535 | 32.923 | 535 | 21.815 |
| 535.5 | 39.987 | 535.5 | 32.537 | 535.5 | 21.545 |
| 536 | 39.407 | 536 | 32.104 | 536 | 21.272 |
| 536.5 | 38.847 | 536.5 | 31.654 | 536.5 | 21.023 |
| 537 | 38.353 | 537 | 31.21 | 537 | 20.783 |
| 537.5 | 37.905 | 537.5 | 30.766 | 537.5 | 20.511 |
| 538 | 37.458 | 538 | 30.305 | 538 | 20.181 |
| 538.5 | 36.99 | 538.5 | 29.824 | 538.5 | 19.81 |
| 539 | 36.493 | 539 | 29.353 | 539 | 19.441 |
| 539.5 | 35.946 | 539.5 | 28.931 | 539.5 | 19.101 |
| 540 | 35.33 | 540 | 28.564 | 540 | 18.785 |

| | | | | | |
|---|---|---|---|---|---|
| 540.5 | 34.658 | 540.5 | 28.211 | 540.5 | 18.474 |
| 541 | 33.982 | 541 | 27.821 | 541 | 18.16 |
| 541.5 | 33.348 | 541.5 | 27.377 | 541.5 | 17.848 |
| 542 | 32.757 | 542 | 26.89 | 542 | 17.541 |
| 542.5 | 32.18 | 542.5 | 26.368 | 542.5 | 17.237 |
| 543 | 31.6 | 543 | 25.81 | 543 | 16.935 |
| 543.5 | 31.018 | 543.5 | 25.213 | 543.5 | 16.639 |
| 544 | 30.442 | 544 | 24.597 | 544 | 16.354 |
| 544.5 | 29.88 | 544.5 | 24.005 | 544.5 | 16.075 |
| 545 | 29.349 | 545 | 23.486 | 545 | 15.787 |
| 545.5 | 28.857 | 545.5 | 23.048 | 545.5 | 15.482 |
| 546 | 28.367 | 546 | 22.65 | 546 | 15.165 |
| 546.5 | 27.815 | 546.5 | 22.234 | 546.5 | 14.85 |
| 547 | 27.165 | 547 | 21.782 | 547 | 14.548 |
| 547.5 | 26.448 | 547.5 | 21.326 | 547.5 | 14.259 |
| 548 | 25.742 | 548 | 20.887 | 548 | 13.978 |
| 548.5 | 25.113 | 548.5 | 20.45 | 548.5 | 13.707 |
| 549 | 24.57 | 549 | 19.986 | 549 | 13.45 |
| 549.5 | 24.075 | 549.5 | 19.497 | 549.5 | 13.209 |
| 550 | 23.58 | 550 | 19.006 | 550 | 12.966 |
| 550.5 | 23.071 | 550.5 | 18.535 | 550.5 | 12.691 |
| 551 | 22.551 | 551 | 18.092 | 551 | 12.376 |
| 551.5 | 22.014 | 551.5 | 17.685 | 551.5 | 12.047 |
| 552 | 21.458 | 552 | 17.319 | 552 | 11.74 |
| 552.5 | 20.913 | 552.5 | 16.986 | 552.5 | 11.469 |
| 553 | 20.422 | 553 | 16.671 | 553 | 11.225 |
| 553.5 | 20 | 553.5 | 16.354 | 553.5 | 10.991 |
| 554 | 19.616 | 554 | 16.024 | 554 | 10.758 |
| 554.5 | 19.232 | 554.5 | 15.679 | 554.5 | 10.522 |
| 555 | 18.831 | 555 | 15.325 | 555 | 10.281 |
| 555.5 | 18.421 | 555.5 | 14.978 | 555.5 | 10.038 |
| 556 | 18.017 | 556 | 14.662 | 556 | 9.806 |

| | | | | | |
|---|---|---|---|---|---|
| 556.5 | 17.634 | 556.5 | 14.384 | 556.5 | 9.608 |
| 557 | 17.28 | 557 | 14.123 | 557 | 9.454 |
| 557.5 | 16.948 | 557.5 | 13.852 | 557.5 | 9.326 |
| 558 | 16.63 | 558 | 13.56 | 558 | 9.192 |
| 558.5 | 16.331 | 558.5 | 13.251 | 558.5 | 9.025 |
| 559 | 16.058 | 559 | 12.931 | 559 | 8.825 |
| 559.5 | 15.805 | 559.5 | 12.615 | 559.5 | 8.613 |
| 560 | 15.543 | 560 | 12.324 | 560 | 8.416 |
| 560.5 | 15.249 | 560.5 | 12.073 | 560.5 | 8.244 |
| 561 | 14.929 | 561 | 11.852 | 561 | 8.09 |
| 561.5 | 14.605 | 561.5 | 11.636 | 561.5 | 7.94 |
| 562 | 14.3 | 562 | 11.416 | 562 | 7.786 |
| 562.5 | 14.023 | 562.5 | 11.204 | 562.5 | 7.637 |
| 563 | 13.764 | 563 | 11.009 | 563 | 7.506 |
| 563.5 | 13.51 | 563.5 | 10.824 | 563.5 | 7.392 |
| 564 | 13.244 | 564 | 10.634 | 564 | 7.276 |
| 564.5 | 12.955 | 564.5 | 10.436 | 564.5 | 7.143 |
| 565 | 12.653 | 565 | 10.232 | 565 | 6.996 |
| 565.5 | 12.372 | 565.5 | 10.025 | 565.5 | 6.853 |
| 566 | 12.14 | 566 | 9.824 | 566 | 6.72 |
| 566.5 | 11.946 | 566.5 | 9.64 | 566.5 | 6.592 |
| 567 | 11.743 | 567 | 9.474 | 567 | 6.468 |
| 567.5 | 11.495 | 567.5 | 9.32 | 567.5 | 6.352 |
| 568 | 11.206 | 568 | 9.174 | 568 | 6.246 |
| 568.5 | 10.913 | 568.5 | 9.033 | 568.5 | 6.139 |
| 569 | 10.654 | 569 | 8.889 | 569 | 6.019 |
| 569.5 | 10.448 | 569.5 | 8.732 | 569.5 | 5.879 |

| | | | | | |
|---|---|---|---|---|---|
| 570 | 10.294 | 570 | 8.559 | 570 | 5.731 |
| 570.5 | 10.169 | 570.5 | 8.375 | 570.5 | 5.601 |
| 571 | 10.038 | 571 | 8.189 | 571 | 5.502 |
| 571.5 | 9.88 | 571.5 | 8.01 | 571.5 | 5.429 |
| 572 | 9.697 | 572 | 7.843 | 572 | 5.354 |
| 572.5 | 9.505 | 572.5 | 7.684 | 572.5 | 5.256 |
| 573 | 9.316 | 573 | 7.529 | 573 | 5.138 |
| 573.5 | 9.138 | 573.5 | 7.383 | 573.5 | 5.019 |
| 574 | 8.976 | 574 | 7.254 | 574 | 4.915 |
| 574.5 | 8.827 | 574.5 | 7.147 | 574.5 | 4.833 |
| 575 | 8.686 | 575 | 7.063 | 575 | 4.766 |
| 575.5 | 8.551 | 575.5 | 7 | 575.5 | 4.707 |
| 576 | 8.427 | 576 | 6.949 | 576 | 4.65 |
| 576.5 | 8.316 | 576.5 | 6.884 | 576.5 | 4.589 |
| 577 | 8.204 | 577 | 6.777 | 577 | 4.524 |
| 577.5 | 8.077 | 577.5 | 6.619 | 577.5 | 4.452 |
| 578 | 7.937 | 578 | 6.435 | 578 | 4.373 |
| 578.5 | 7.791 | 578.5 | 6.258 | 578.5 | 4.286 |
| 579 | 7.637 | 579 | 6.111 | 579 | 4.195 |
| 579.5 | 7.462 | 579.5 | 5.996 | 579.5 | 4.107 |
| 580 | 7.269 | 580 | 5.896 | 580 | 4.029 |
| 580.5 | 7.087 | 580.5 | 5.797 | 580.5 | 3.965 |
| 581 | 6.949 | 581 | 5.698 | 581 | 3.914 |
| 581.5 | 6.858 | 581.5 | 5.605 | 581.5 | 3.866 |
| 582 | 6.787 | 582 | 5.519 | 582 | 3.812 |
| 582.5 | 6.697 | 582.5 | 5.432 | 582.5 | 3.746 |
| 583 | 6.571 | 583 | 5.338 | 583 | 3.668 |
| 583.5 | 6.418 | 583.5 | 5.242 | 583.5 | 3.589 |
| 584 | 6.256 | 584 | 5.156 | 584 | 3.521 |
| 584.5 | 6.098 | 584.5 | 5.082 | 584.5 | 3.465 |
| 585 | 5.946 | 585 | 5.009 | 585 | 3.413 |
| 585.5 | 5.804 | 585.5 | 4.931 | 585.5 | 3.353 |

| | | | | | |
|---|---|---|---|---|---|
| 586 | 5.68 | 586 | 4.846 | 586 | 3.288 |
| 586.5 | 5.58 | 586.5 | 4.759 | 586.5 | 3.226 |
| 587 | 5.495 | 587 | 4.665 | 587 | 3.173 |
| 587.5 | 5.408 | 587.5 | 4.558 | 587.5 | 3.125 |
| 588 | 5.307 | 588 | 4.435 | 588 | 3.071 |
| 588.5 | 5.186 | 588.5 | 4.308 | 588.5 | 3.009 |
| 589 | 5.055 | 589 | 4.196 | 589 | 2.949 |
| 589.5 | 4.931 | 589.5 | 4.114 | 589.5 | 2.902 |
| 590 | 4.831 | 590 | 4.067 | 590 | 2.871 |
| 590.5 | 4.76 | 590.5 | 4.045 | 590.5 | 2.847 |
| 591 | 4.706 | 591 | 4.028 | 591 | 2.818 |
| 591.5 | 4.648 | 591.5 | 3.993 | 591.5 | 2.78 |
| 592 | 4.575 | 592 | 3.924 | 592 | 2.737 |
| 592.5 | 4.492 | 592.5 | 3.823 | 592.5 | 2.697 |
| 593 | 4.402 | 593 | 3.709 | 593 | 2.663 |
| 593.5 | 4.307 | 593.5 | 3.606 | 593.5 | 2.636 |
| 594 | 4.21 | 594 | 3.526 | 594 | 2.609 |
| 594.5 | 4.12 | 594.5 | 3.469 | 594.5 | 2.576 |
| 595 | 4.047 | 595 | 3.428 | 595 | 2.536 |
| 595.5 | 3.997 | 595.5 | 3.394 | 595.5 | 2.494 |
| 596 | 3.96 | 596 | 3.36 | 596 | 2.461 |
| 596.5 | 3.917 | 596.5 | 3.319 | 596.5 | 2.443 |
| 597 | 3.862 | 597 | 3.267 | 597 | 2.433 |
| 597.5 | 3.798 | 597.5 | 3.208 | 597.5 | 2.416 |
| 598 | 3.727 | 598 | 3.153 | 598 | 2.378 |
| 598.5 | 3.652 | 598.5 | 3.114 | 598.5 | 2.318 |
| 599 | 3.576 | 599 | 3.091 | 599 | 2.243 |
| 599.5 | 3.511 | 599.5 | 3.073 | 599.5 | 2.166 |
| 600 | 3.47 | 600 | 3.054 | 600 | 2.102 |

TABLE 2

| | | | |
|---|---|---|---|
| | µg/ml | 0.2 | 0.6 | A |
| 1140 | SUM OF INTENSITIES FROM 538 TO 560 nm | 923 | 616 | B |
| 545 | SUM OF INTENSITIES FROM 560 TO 590 nm | 444 | 303 | C |
| 2.090 | B\C | 2.078 | 2.037 | D |
| 1 | B+C\100%B+C | 0.81 | 0.55 | E |
| 1685 | B+C | 1367 | 919 | F |
| 4080 | SUM FROM MEASURED EMISSION MAXIMUM | 3308 | 2207 | G |
| 0.781673 | SUM FROM EMISSION MAXIMUM/SUM TOTAL | 0.782952 | 0.785718 | H |
| 1 | SUM ALL INTENSITIES/SUM OF ALL INTENSITIES AT 100% FLUORESCENCE | 0.809410 | 0.538181 | I |
| 1 | EMISSION MAXIMUM/EMISSION MAXIMUM AT 100% FLUORESCENCE | 0.802496 | 0.525404 | J |
| 5220 | INTENSITY SUMS OF ENTIRE SPECTRA | 4225 | 2809 | K |
| 48.475 | INTENSITY AT 513nm | 38.901 | 25.469 | L |

METHOD FOR DETERMINING THE DEGREE OF SPECTRAL INTERFERENCE IN AN ASSAY HAVING A TEST SAMPLE

BACKGROUND OF THE INVENTION

1. Field of the Invention

The present invention relates to the field of scientific research instrumentation and, in particular, to fluorescence spectroscopy. The present invention includes a method that allows the utilization of fluorescent tracers in techniques where previously only radioactive tracers could be used. For example, the present invention is applied in fluorescent techniques to test for the presence of an enzyme inhibitor in a crude extract or otherwise spectrally interfering substance.

2. Description of the Prior Art

There is no known method for spectral interference correction applied to fluorescence spectroscopy, except for applicant's copending application Ser. No. 08/148,731, filed on Oct. 29, 1993, titled: A Fluorescent Assay and Method That Corrects For Spectral Interference, which is incorporated by reference, that relates to a method that incorporates a separate or additional fluorescent label into the fluorescent assay. The additional label is unique in that it acts as a measure of interference caused by a colored or otherwise spectrally interfering compound. The present invention, however, eliminates the use of the additional label and, is applied to the primary fluorescent label in the assay.

An article entitled: Use of Fluorescent Cholesteryl Ester Microemulsions In Cholesteryl Ester Transfer Protein Assays by Charles L. Bisgaier, Laura Minton, Arnold D. Essenberg, Andrew White, and Reynold Homen published in the Journal of Lipid Research, Volume 34, 1993, discloses a fluorescent method that measures the activity of lipid transfer protein. The authors point out the limited use of their method due to spectral interference caused by the presence of colored compounds.

The present method is readily applicable to any fluorimeter and restores accuracy to fluorometric measurements in the presence of compounds that may otherwise prevent accurate measurement.

The present invention accomplishes this without the use additional substrates, utilizing standard laboratory equipment.

SUMMARY OF THE INVENTION

It is a principal object of this invention to provide a method of data analysis for accurate determination of enzyme activity utilizing fluorescence, in a sample that would otherwise yield inaccurate results due to spectrally interfering components.

It is another object of the present invention to provide such a method for individuals in the field for the purpose of determining the activity of an enzyme in the presence of a potential inhibitor.

It is still another object of the present invention to provide such a device that is accurate and without utilization of radioisotopes.

It is yet another object of the present invention to provide a new method to measure conventional spectrophotometric assays in a fluorimeter instead of an absorption spectrometer and thus increasing sensitivity of the conventional assay.

To the accomplishments of the foregoing objects and advantages, the present invention, in brief summary, comprises a method that accurately determines the change in fluorescence of a fluorescent measurement without regard to the presence of colored or otherwise interfering factors.

BRIEF DESCRIPTION OF THE DRAWINGS

The foregoing and still other objects and advantages of the present invention will be more apparent from the following detailed explanation of the preferred embodiments of the invention in connection with the accompanying drawings wherein:

FIG. 12 consists of FIGS. 12A and 12B and is table 1 of raw data; and FIG. 13 is table 2 that lists derived quantities based on the present invention.

DESCRIPTION OF THE PREFERRED EMBODIMENTS

Figure 1:
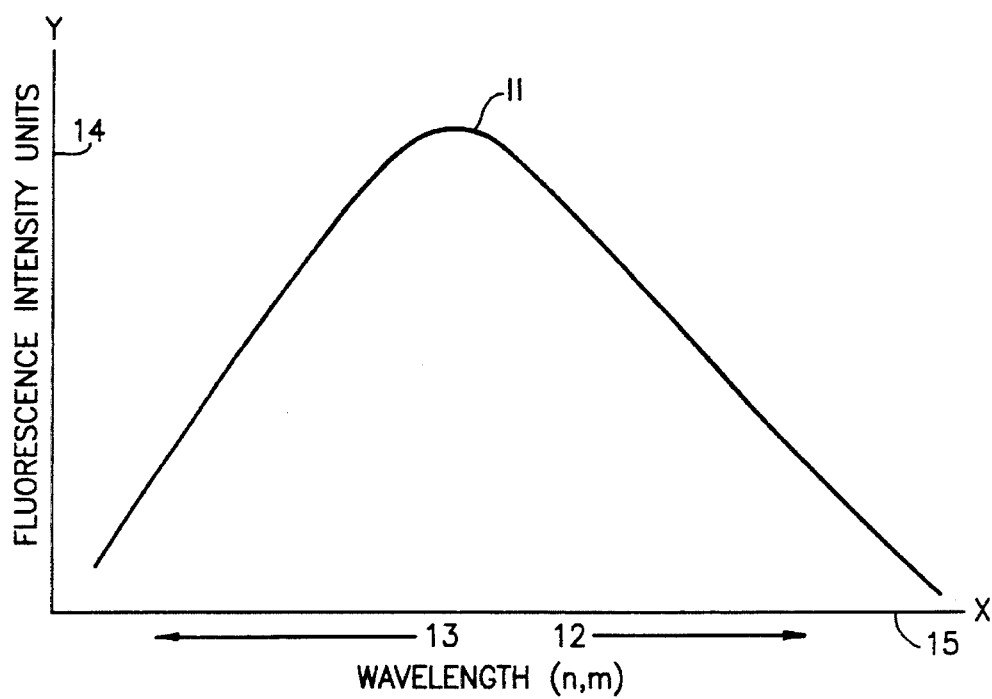
FIG. 1 is an intensity versus wavelength representation of the emission spectra from a fluorescent label.

Fluorescence spectroscopy is a technique that involves the measurement of light intensity emitted from a fluorescent label. The fluorescent label is excited by an excitation light source at a specific wavelength. Once excited, the label decays to a less energetic state. The energy decay may take several pathways, one of which is emission of light energy. Other pathways include radiationless decay which dissipates the energy of the excited state without light emission. The capability of a fluorescent label to dissipate the energy of its excited state either through light emission or pathways that yield little to no light emission is a property that is often related to the molecular environment of the fluorescent label. The modulation of emission by the molecular environment is utilized in scientific research to follow the label through a chemical reaction or to measure the activity of an enzyme.

For example, if a particular fluorescent label, –NBD, transfers the energy of its excited state to other NB molecules without light emission, measurement of florescence from a sample containing many NBDs yields very little fluorescence. If an enzyme that separated the NBD fluorescent labels was added, an increase in fluorescent emission intensity per unit time would be measured from the sample. The fluorescent emission intensity would continue to increase as the enzyme continued to work separating the NBDs. This fluorescent technique would then be measuring the activity of the hypothetical enzyme by measuring the increase in emission intensity over a period of time. This is a conventional scheme for enzyme activity measurement and would be implemented in a fluorimeter. The measurement of emission intensity would be made at the known emission maximum of the label. The emission maximum is the wavelength of the emission spectra that gives the highest intensity, i.e. the brightest light. Although the conventional method works fine when the assay conditions are among pure components, in practice, the conventional method is of limited value when the fluorescent technique is applied to unknown or impure samples.

The accuracy of the conventional technique is dependent upon the fluorimeter's ability to measure the intensity at the emission maximum of the label. For example, if the enzyme of interest was found in bacteria indigenous to murky pond water and the bacteria fed on particulate matter that contributed to murkiness, one would expect the enzyme activity to be greatest in the murkiest pond water. In a conventional fluorescent enzyme activity assay, the scientist would take samples of different pond water at equal volumes with a negative control of pure distilled water and a positive control of pure enzyme. Each sample would be placed in a different tube and incubated with the fluorescent label that measured the enzyme activity. The samples would then be read in a fluorimeter at the emission maximum of the label. The results would be falsely interpreted as enzyme activity decreasing or remaining the same with an increase in murkiness of pond water. The false result is indicative of spectral interference derived from the murkiness of the mixture regardless of enzyme activity affecting the fluorescent label.

The present invention allows the scientist to determine the degree of a spectral interference in a fluorescent system. Accomplishing this, the invention provides a method for determining the concentration of colored components or degree of turbidity in a fluorescent assay system. Briefly, the invention includes the examination of the entire emission spectra of the fluorescent label rather than only the emission maximum. Furthermore, the provisions for determining the concentration of colored compound or turbidity are also applied to conventional calorimetrical or turbidimetric assays by utilizing a fluorimeter to increase sensitivity over absorbance spectrometry.

For example, the emission spectra may be represented by a graph FIG. 1, where the Y-axis 14 is emission intensity and the X-axis 15 is wavelength of light. The highest intensity is at the emission maximum 11 and the longer wavelengths of light are in direction 12 and the shorter wavelengths of light are in direction 13. Since the frequency of light multiplied by its wavelength is equal to a constant, the light associated with the emission spectra in direction 12 (away from the Y axis) or increasing wavelength, is light of decreasing frequency and decreasing energy. Conversely, because the light associated with direction 13 of FIG. 1, is of decreasing wavelength, the light of direction 13 is of increasing energy.

Figure 2:
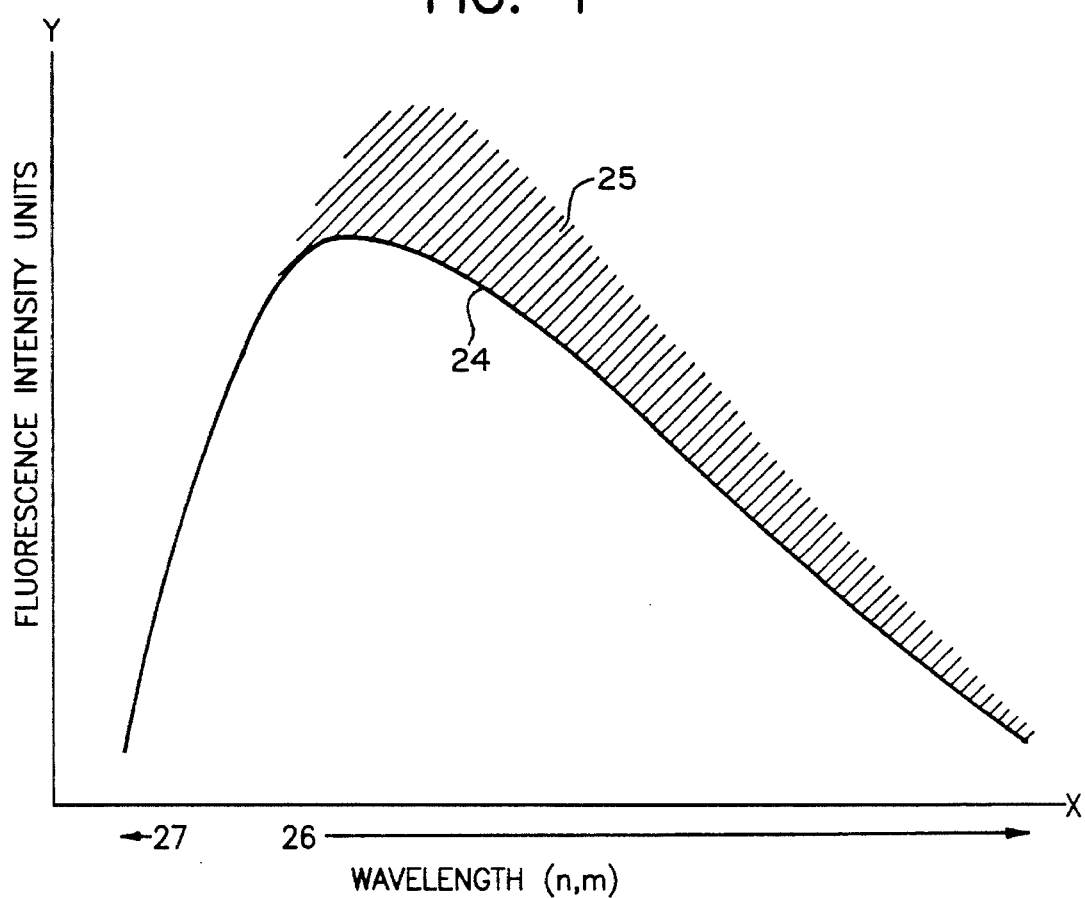
FIG. 2 is a comparison of emission spectra of a sample with spectral interference and a sample without spectral interference.

In FIG. 2., a murky sample 24 is illustrated and compared with a non-murky sample by way of shaded area 25. The total light intensity is attenuated as seen from line 24 and there is more of an affect on the emission wavelengths associated with lower energy 26 than from those associated with higher energy 27. This murky example 24 is analogous to a fluorescent sample in the presence of a colored compound that absorbs the emitted light normally measured by the fluorimeter. A turbid sample would have a similar attenuated emission spectra.

The observation that spectral interference from a number of different sources has a greater effect on the low energy region of the emission spectra is utilized by the present invention. The ratio of the sum of intensities in the low energy region to the sum of intensities in the high energy region is linearly related to the attenuation of the intensity at the emission maximum. In addition, the sum of intensities from an arbitrarily selected wavelength in the emission spectrum to a lower energy wavelength divided by the sum of a collection of wavelengths at even a lower energy region is linearly related to spectral interference. In order to characterize spectral interference and to relate interfering effects to attenuation of the emission maximum, measurements are made on samples containing known quantities of spectrally interfering component in increasing concentration. A proportionality of low energy region intensities to high energy region intensities is determined for each concentration and together expressed in terms of each respective emission maximum. This is accomplished using an equation that represents the line formed between a term indicative of the emission maximum (Y) and the ratio of low energy to high energy intensities (X) by (Y)=M(X)+B, where M is the slope of the line defined as the change in Y per change in X $\Delta Y/\Delta X$) or $(Y2-Y1)/(X2-X1)$) and B is a constant. The equation is solved for M and B by substitution of the X,Y pairs for two concentrations of the interfering component. Next, the unknown sample is measured and the proportionality of low energy region per high energy region is determined based on the same wavelengths as the known samples. Once determined, the low to high ratio is substituted as the X value in the equation of the line derived from the known samples. The equation is solved for the Y value, which is indicative of the true emission maximum intensity. The method of the invention may also be expressed graphically.

Figure 3:
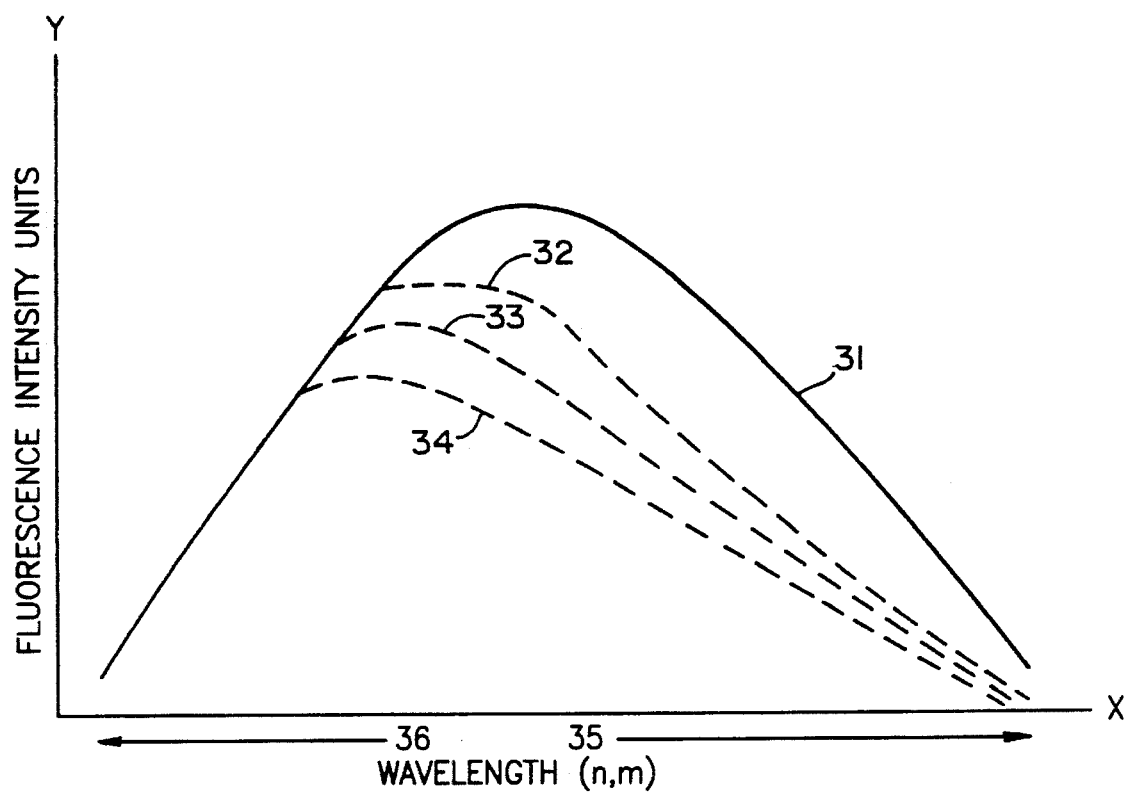
FIG. 3 is an emission intensity versus wavelength illustration of four samples three with spectral interference.

In FIG. 3, for example, the emission spectra of four different fluorimeter emission spectra reads on the same set of axis are depicted by solid line 31 and broken lines 32, 33 and 34. These four emission spectra represent known quantities, in increasing amounts, of spectrally interfering substance in the sample. Specifically, they start from no interference, solid line 31, to the highest level of interference, broken line 34. The degree of spectral interference, according to the present invention, with each known amount of spectrally interfering component in the sample is used as a template to determine unknown amounts of interference in a sample. The unknown amount of spectrally interfering substance and its effect on the emission maximum is determined by measuring the intensity of the low energy wavelengths per intensity of high energy wavelengths at each known quantity of interfering component and comparing this ratio to that of the unknown. The relationship of these values is determined by an easily expressible means to enable a sample with unknown concentration of interfering component to be evaluated in a similar manner and a determination of the unknown concentration of interfering component is made according to the known concentrations.

Figure 4:
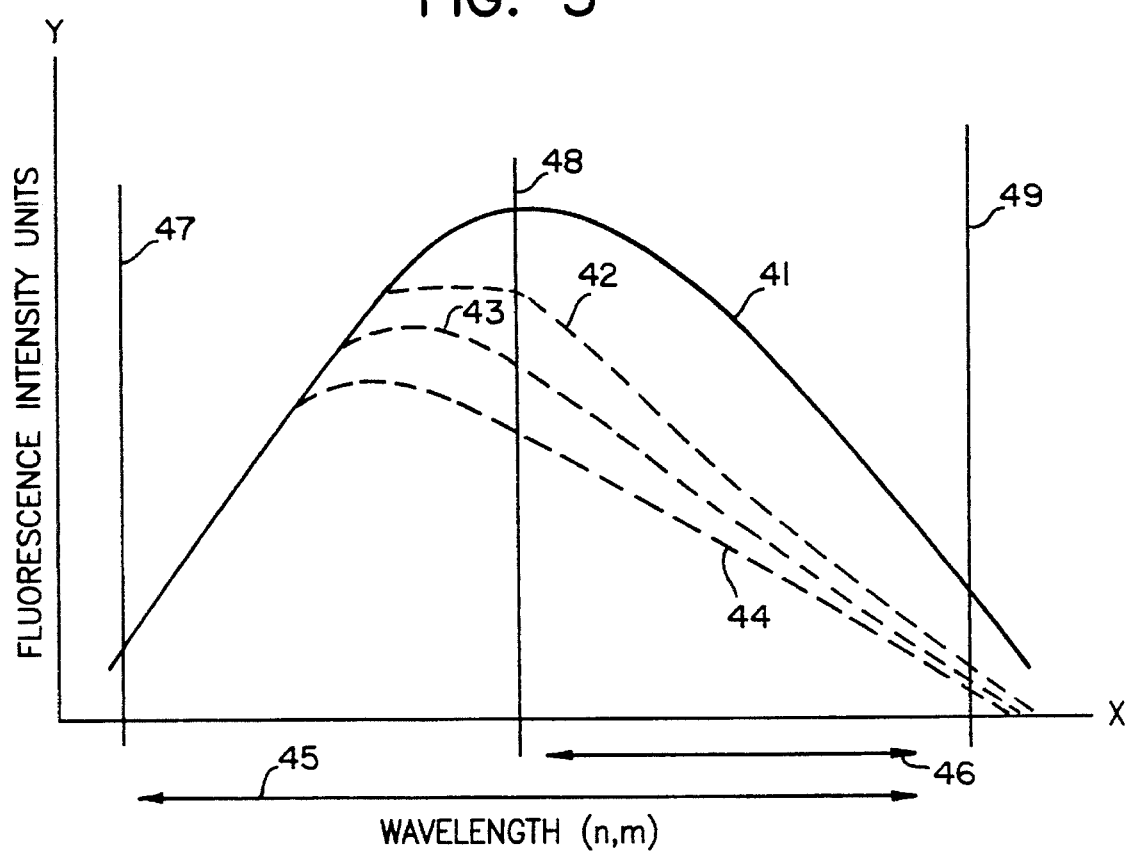
FIG. 4 is an emission intensity versus wavelength depiction of four samples one without and three with spectral interference configured for the present invention.

For example, one convenient means of expressing the effect of an interfering component is depicted in FIG. 4. The emission spectra readings 41, 42, 43 and 44 are, as in FIG. 3, known quantities of interfering component added to a fluorescent compound in increasing amounts. Line 41 represents the pure fluorescent label and line 42 represents the addition of a known quantity of a spectrally interfering compound to the pure label. Line 43 is a further increasing amount of spectrally interfering compound added to pure label or an amount of interfering compound greater than 42, and line 44 is still a further increasing amount of spectrally interfering compound added to pure label or an amount greater than the former.

The wavelengths of light within boundaries 47, 48 and 49 are to be treated as those associated with energy regions. The wavelengths between boundaries 48 and 49 represent the low energy region and the wavelengths between 47 and 48 represent the high energy region.

The intensities (i.e. values on the Y axis) for each point of line or pure label 41 between boundaries 48 and 49 are summed which represents the low energy portion of the spectrum at zero interference or 100% measurable fluorescence. Similarly, the intensities on line 41 between boundaries 47 and 49 are summed, representing both high and low energies of light. The summed quantities will be referred to as 45 and 46, respectively, for line 41.

The total intensity sum 45 for line 44 divided by the sum 45 for line 41 gives the relative attenuation or the efficiency of fluorescence detection of the pure label by the most severely interfered line 41. The total intensity sum 45 for line 43 divided by the sum 45 for line 41 gives the efficiency of fluorescence detection relative to the pure label of the line 43. Likewise, the sum 45 for line 42 divided by the sum 45 for line 41 gives the relative attenuation or efficiency to the pure label of the line 42. The relative attenuation will indicate how much interfering compound is present or how much label is truly fluorescing but not detected. The relative attenuation is equated to the intensity sums already determined by utilizing the ratio of low energy intensity to high energy intensity.

Figure 5:
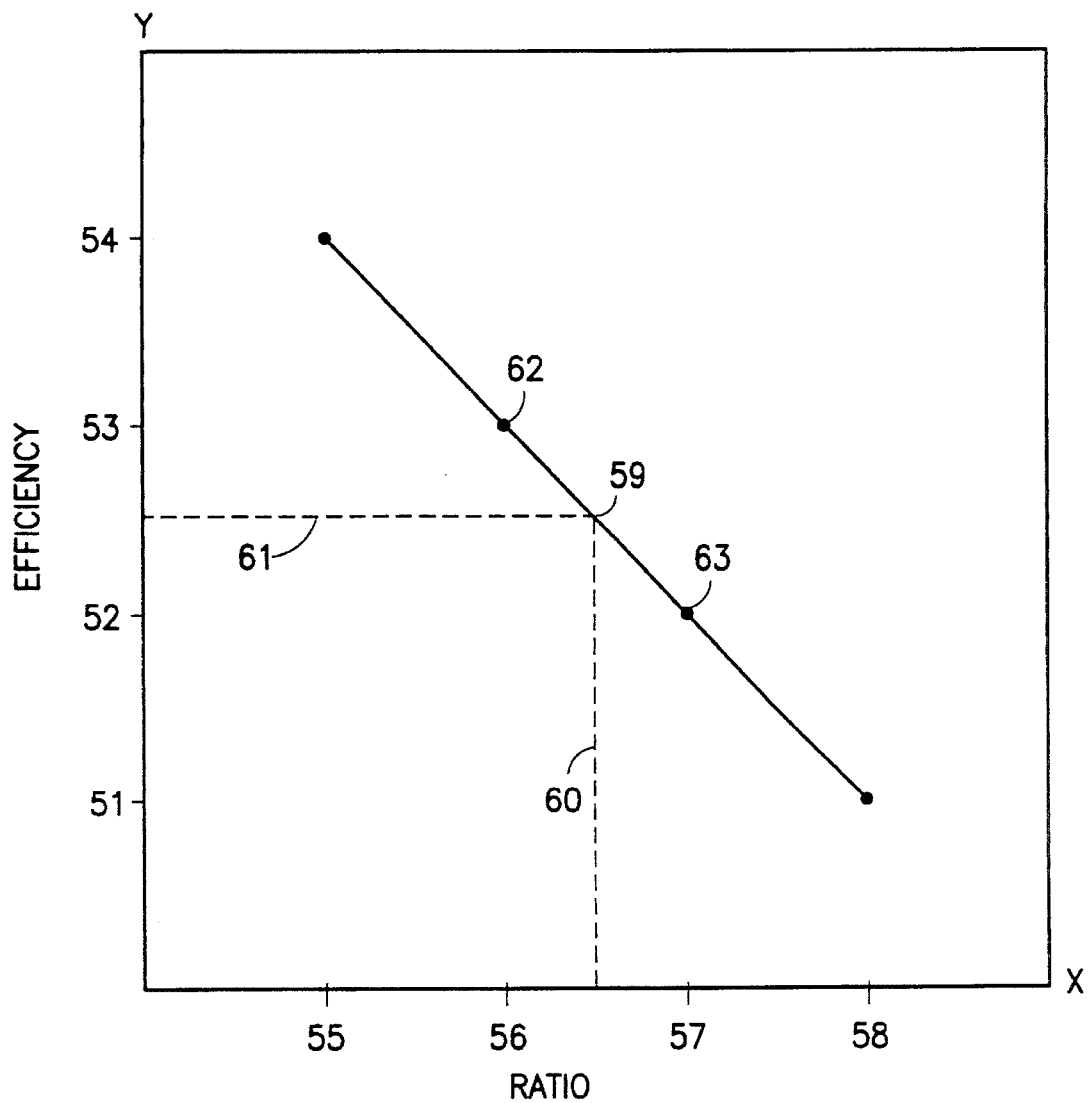
FIG. 5 is a plot of the relationship between high and low energy regions and attenuation of emission maximum used by the present invention.

For example, from line 44 one would divide low energy intensity sum 46 by total intensity sum 45 and utilize the result as an X value. The Y value would be total intensity sum 45 for line 44 divided by sum 45 for line 41. Repeating this for lines 43, 42 and 41 would allow the plot drawn in FIG. 5. The Y axis point 54 represents zero interference. The X-axis point 55 is the sum 46 divided by sum 45 of line 41 of FIG. 4. Similarly, the X axis points 56, 57, 58 represent sum 46 divided by sum 45 of lines 42, 43 and 44, respectively of FIG. 4. The Y axis points 53, 52, 51 represent percentages of less than pure label. Once this relationship is determined, a sample with unknown interference is similarly analyzed and summed at high and low energy areas, a ratio determined, and the value 60 is plotted on the sloped line of FIG. 5 at 59. A corresponding Y value 61 is determined for the unknown. If this value is, for example, 0.4 then it is known the sample is 60% attenuated from the true florescent intensity at the emission maximum. Alternatively, the point 60 is determined from the equation of the line Y=MX+B that connects 62 and 63. For example, if the Y axis point 52 is a known sample at 0.5 (half that of the pure label) and X axis point 57 is the sum ratio of 40/100 or 0.4, and Y axis point 53 is 0.35 and X axis point 56 is 0.33 from a sum ratio of 30/90, then the slope can be calculated using the equation $M=(Y_2-Y_1)/(X_2-X_1)$. Solving for B, gives the values for the equation of the line. B may be equated to Y-MX, and by using values associated with the 100% efficiency point, Y would equal 1 making B=-MX. Unknown relative attenuation or efficiency (Y) values may be determined algebraically by substituting M, X and B in Y=MX+B.

The present invention is useful in mass screening projects, such as those performed by pharmaceutical companies in search of drug candidates. For example, a crude extract of a plant or fungal broth is added to an enzyme activity assay to measure the effect, if any, of the extract on enzyme activity. In this type of screening project, it is difficult to utilize a fluorescent system because of spectral interference typically encountered with crude extracts due to color. The dark green color characteristic of plant extracts will absorb light energy of the emission spectra of a fluorescent tracer in an assay system. The attenuation is not a result that is generated by a potential drug candidate's effect on the enzyme tested, but an effect due to a physical property of the compound tested. This problem is pointed out by Bisgaier et al. cited above.

The present invention allows a calculable emission spectrum interference correction factor to be derived from the assay system by analysis of spectrum associated with the label. Furthermore, the invention may be used on instruments that read intensity at only one wavelength.

For simplicity, the present invention is presented with respect to one fluorescent label, N-(7-nitrobenz-2-oxa-1,3-diazol-4-yl)amino (NBD). The invention will, however, be applicable for any fluorescent label where spectral interference is encountered. The analysis of the emission spectra is used as a means to quantify spectral interference regardless of the type of fluorescence assay.

In order to provide complete understanding of the invention and the various techniques used to implement the invention, the following examples are presented.

The present invention provides means for a high throughput application of the disclosed technique. A fluorimeter used for high volume screening will normally only accept samples contained within the wells of a microtiter plate, a 5 inch by 3 inch fixed plate array 12 columns by 8 rows of 96 sample compartments in which the compounds screened for enzyme inhibition are tested. The microtiter plate reading fluorimeter does not have scanning monochromatic to pass excitation source or emission spectra. The instruments are limited to reading one intensity at one wavelength per sample compartment. The instruments are equipped with replaceable filters that allow only a certain bandwidth of light to pass. Conventionally, a plate is placed into the instrument and a single intensity at one apparent wavelength (actually a bandwidth depending upon the quality of the filters) per sample is read. The present invention provides means for extracting the information necessary to calculate spectral interference from these instruments. The method includes fitting several filters in the instrument. For example, to correct the emission maximum of a sample of NBD fluorescent label, with reported emission maximum at 535 nm and excitation wavelength of 465 nm, filters allowing light passage at 515, 535, 560 and 590 nm are fitted into the emission filter wheel. The excitation wheel is fitted with a 465 nm filter. The fluorimeter is programmed or run manually to collect the fluorescence intensity at all four emission wavelengths with one excitation of 465 nm.

Figure 6:
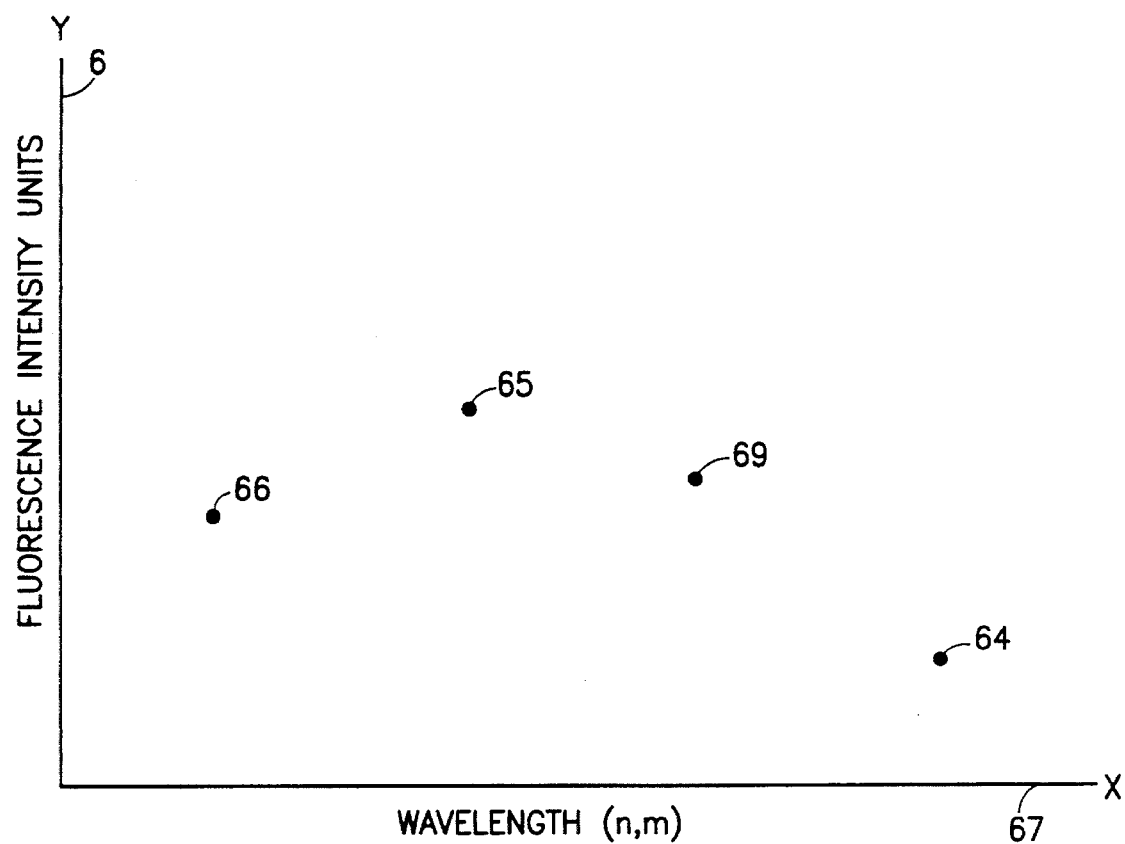
FIG. 6 is an emission intensity versus wavelength depiction from a single wavelength reading instrument according to the present invention.

FIG. 6 further illustrates the improvement over conventional techniques, where the instrument normally is utilized to collect a single wavelength, emission maximum. The invention, however, provides enhanced performance to the instrument. In FIG. 6, the Y axis or intensity 6 and the X axis or wavelength 67 is plotted. Point 66 is a read at 515 nm emission filter, point 65 is a read at 535 nm, point 69 is a read at 560 nm and point 64 is a read at 590 nm.

Figure 7:
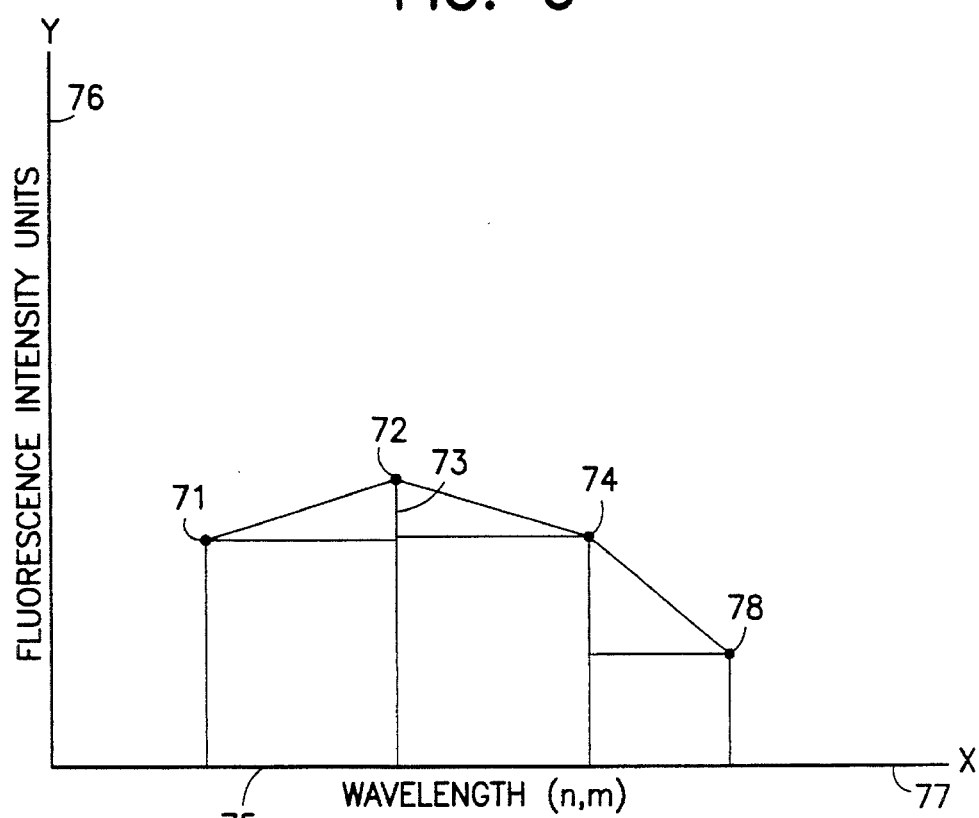
FIG. 7 is an emission intensity versus wavelength depiction from a single wavelength reading instrument with modifications according to the present invention.

FIG. 7 provides a Y axis or intensity 76 versus an X axis or wavelength 77 plot, that illustrates the spectral interference determination technique according to the present invention where the single wavelength read instrument is enhanced to allow analysis of the entire emission spectra. Points 71, 72, 74 and 78 represent single reads at 515 nm, 535 nm, 560 nm and 590 nm, respectively. Intensity by energy region are determined geometrically in terms of areas to enable ratio determination. For example, intensity value 71 multiplied by 75 (the difference in filter wavelengths i.e. 535 nm–515 nm=20) equals the area of the rectangle. Intensity value 72 minus intensity value 71 equals triangle side 73 of which multiplied by (0.5) (20) equals the area of triangle of points 71 and 72.

A similar analysis is performed to calculated the entire areas for sum ratios. The measurements are applied as in FIG. 5 for determination of unknown samples.

Figure 8:
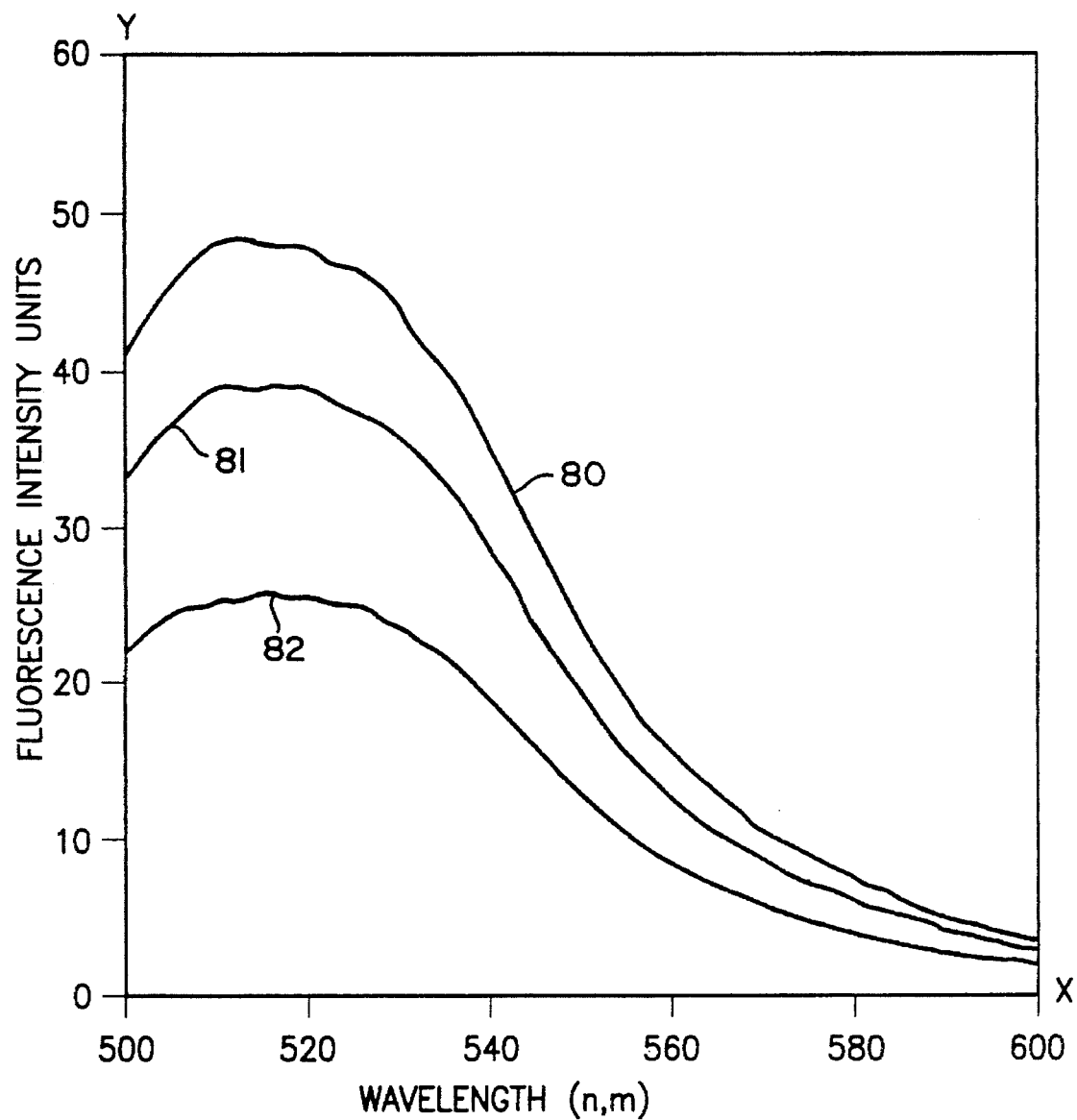
FIG. 8 is an emission intensity versus wavelength plot generated by a fluorimeter for use in the present invention.

The present invention may be applied in techniques, all of which are based on the analysis of high and low energy regions in the emission spectra for correction of emission maximum. For example, table 1, shown in FIGS. 12A and 12B, represents raw data generated by a Perkin-Elmer LS50 fluorimeter. FIG. 8 depicts a graphical representation of the data in table 1. Table 2, shown in FIG. 13, includes several variations of the present invention all involving comparisons of low and high energy areas using the raw data of table 1. Table 2, based on the raw data, lists derived quantities, according to the present invention, line A represents the final concentration in micrograms per milliliter of a spectrally interfering compound added to a fluorescent label. Line B represents the sum of intensities from the reported emission maximum (538 nm) of the label to an arbitrary point (560 nm) in the low energy area of the emission spectrum. Line C represents the sum of intensities from the arbitrary point (560 nm) to another arbitrary point (590) further into the low energy region of the emission spectrum. Line D is B divided by C. Line E is a determination of fluorescent efficiency which is an indication how efficiently the instrument is detecting the emission spectrum of the label this was previously described as relative attenuation. The values are derived from the sum of the intensities between the reported emission maximum of the label and the first arbitrary point (538 nm to 560 nm) picked for line B, divided by line B for the sample at 0 ug/ml of interfering compound or the 100% efficiency sample. Line F is the sum of all the intensities from the wavelength of the reported emission maximum to the second arbitrarily picked point, this is equal to line B plus line C. Line G is the summation of the intensities starting at the wavelength of the measured emission maximum of the 0 mg/ml sample (512.5 nm), for all samples. Line H is the summation of the intensities starting at the wavelength determined to be the emission maximum of the 0 ug/ml for all samples divided by the sum of all wavelengths in each sample. Line I is the sum of all the intensities from 500 to 600 nm divided by the intensities from 500 to 600 nm of the 0 ug/ml sample. This provides an alternate to measuring efficiency relative to pure label. Line J represents the intensity of each sample at the wavelength of the measured emission maximum of the pure sample divided by the measured emission maximum of the pure sample. This provides another method of determining efficiency relative to a sample without spectral interference. Line K is the summation of all intensities in each respective spectrum. Line L is the intensity at the wavelength of the measured emission maximum of the pure label. All the methods of efficiency determination are in agreement as are the plots to support the method in general.

The following examples illustrate the method according to the present invention and include some variation to the technique. FIG. 8 is a intensity versus wavelength plot of columns 1, 2 and 3 of table 1. Plot 80 represents the intensities at wavelengths for column 1 of table 1 which is a sample that does not contain spectrally interfering compound or 0 ug/ml concentration of spectrally interfering compound. The emission intensities are measured at wavelengths from 500 nm to 600 nm. The measured emission maximum is at point 4 or 513 nm of table 1. Plot 81 of FIG. 8 represents the values in column 2 of table 1 that are the intensities emitted from a sample with a concentration of 0.2 ug/ml of spectrally interfering compound. Plot 82 of FIG. 8 represents the data of column 3 in table 1 which contains 0.6 ug/ml of spectrally interfering compound.

Figure 9:
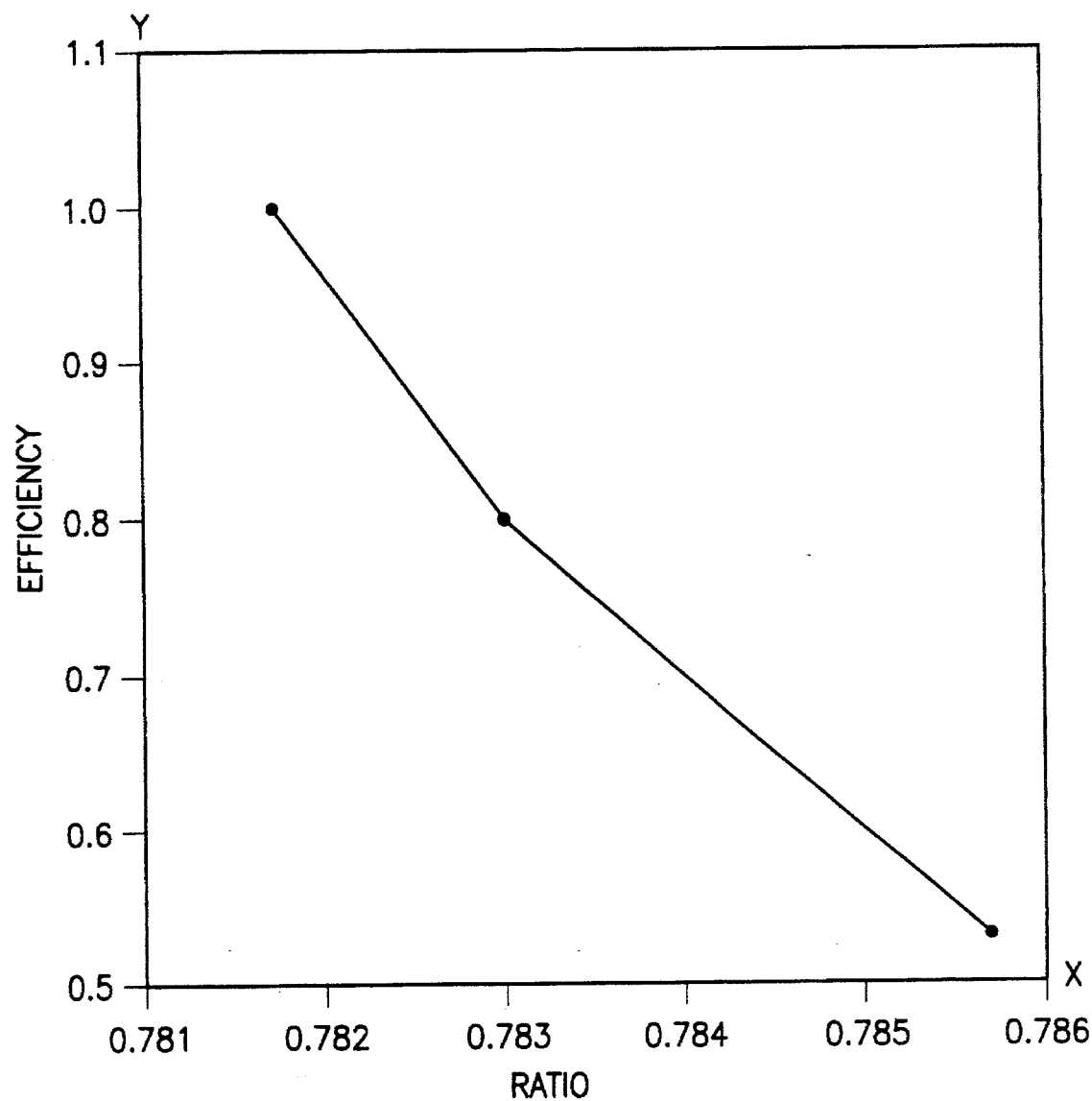
FIG. 9 is a plot of a data ratio versus efficiency according to the present invention.

FIG. 9 is a plot that has been presented previously with hypothetical data. The method is applied to these actual measurements as follows: the fluorescent label of interest is added to an assay mixture with the conditions of the assay as a negative control, i.e. there should be no enzyme present that changes the intensity of fluorescence nor should there be any unknown compound present that might generate conditions of spectral interference. Column 1 of table 1 is an example of this with emission intensities measured from 500 to 600 nm. The wavelength associated with the maximum emission intensity is selected from column 1 at 513 nm (4) of intensity 48.475 units. Next, to the same or a different sample containing the same amount of label is added a low concentration of colored or otherwise spectrally interfering compound, in the case of column 2 of table 1, the concentration of interfering compound was made to 0.2 ug/ml in the sample. The emission is again read from 500 nm to 600 nm. An increasing amount of compound is again presented to the label under the same conditions and the emission is read (table 1 column 3, 0.6 ug/ml). The emission maximum of the pure label is at 513 nm which becomes the dividing wavelength between high energy and low energy regions for all of the spectra. It will also be demonstrated that it is not a requirement to use the wavelength of the emission maximum of the pure label as the dividing point for the present invention to determine spectral interference. However, the emission maximum of the pure label will be reviewed first and the intensities from 513 nm to 600 nm are summed for the 0, 0.2 and 0.6 ug/ml compound concentrations (line G, table 2). These values represent the low energy region of the emission spectra. The intensities from 500 to 600 nm (line K, table 2) are also summed which include both the high and low energy regions of the spectra. The sum of the low energy region (line G) is divided by the sum of all the intensities (line K). This ratio of low energy intensities to total (line H) is used later to define a linear relationship between the samples. A factor relating the effect of the compound to the attenuation of detected light intensities relative to the pure label is next determined by dividing the sum of the entire collection of emission intensities for each sample by the sum of the intensities from the pure sample. This is a fluorescence detection efficiency term for each sample the values are in line I of table 2.

Next, a relationship between the 0, 0.2 and 0.6 ug/ml samples is derived from the values of line H and the detection efficiency values of line I. The linear relationship is depicted in FIG. 9.

Figure 10:
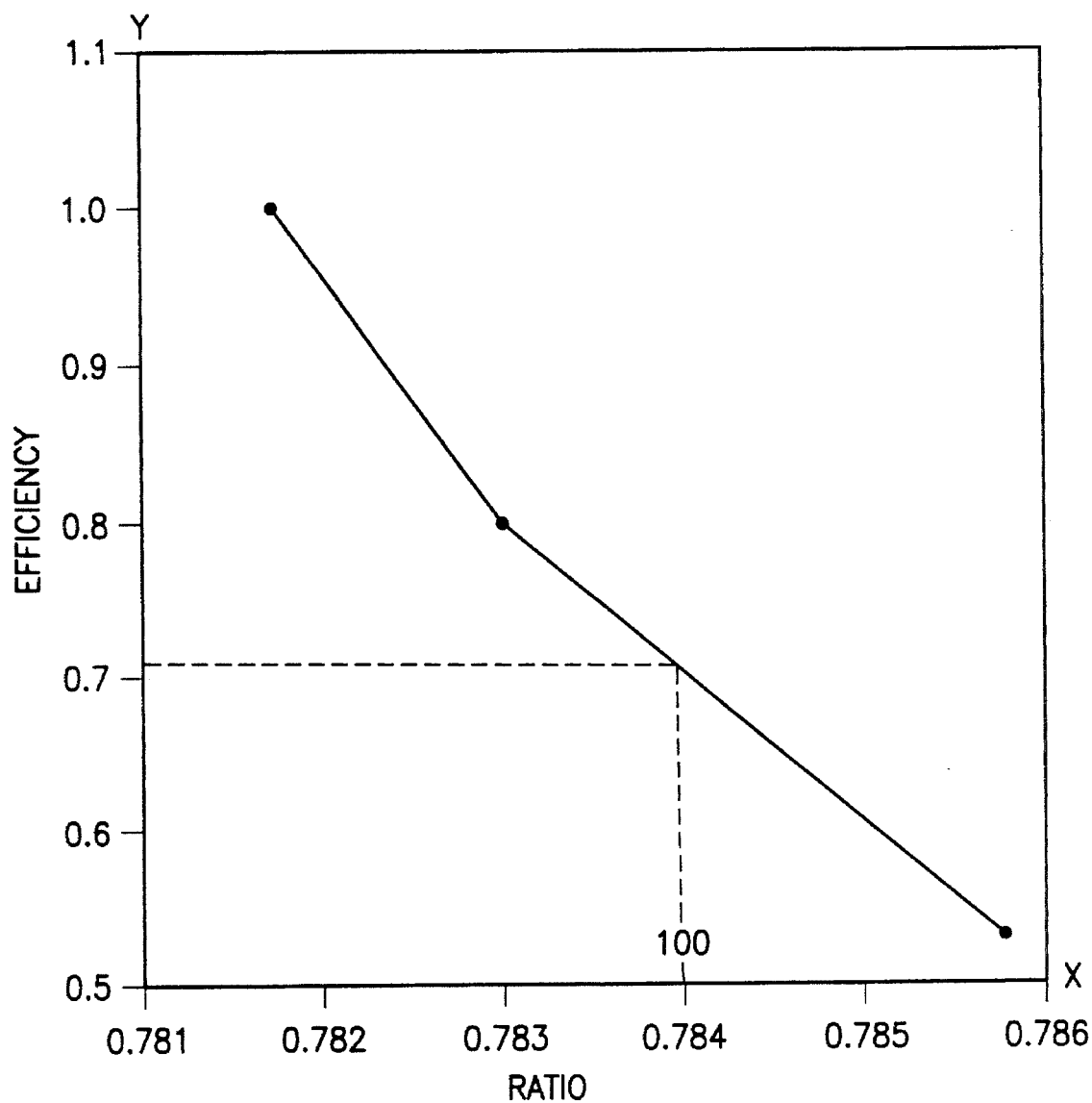
FIG. 10 illustrates a method of extracting information from a data plot according to the present invention.

The method of the present invention is applied to samples that may or may not contain spectrally interfering compounds in the following manner. The sample is read in the fluorimeter under the same conditions as the original set of samples used to generate the graph of FIG. 9. The summation of intensities is similarly made as in lines G and lines K of table 2 and the ratio for each unknown is also determined as in line H. The ratio is applied to the X axis of FIG. 9 and the Y axis is determined by the intersection point of the x value to the line. For example, if the ratio from the unknown sample is determined as 0.784, point 100 of FIG. 10 on the X-axis, the corresponding Y-axis value is approximately 0.7, because the Y-axis values were originally derived as a measurement of efficiency, the unknown sample is actually 70% of the true value. Another practical example involves the testing of crude extracts for enzyme inhibitors, a hypothetical enzyme, such as the enzyme described previously, indigenous to murky pond water tested in a fluorescent method of activity measurement. The activity is measured as an increase in fluorescence intensity per unit time. Although the samples would appear to have reduced activity with increasing murkiness, a calculation of low to high energy applied to FIG. 9 would yield an efficiency that would be taken into account in the final result. For example, if the Y-axis value were 0.7 and the measured intensity value at a certain wavelength equals 30, the true enzyme activity would result from 30/0.7=42.857.

There are other applications of the present invention that improve upon conventional absorption spectrophotometric techniques. For example, methods that utilize absorption spectrometers to measure calorimetry assays for determinations of such things as protein, cholesterol, triglyceride and phospholipid concentration. Conventional methods utilize means of staining a protein or generating a colored compound in response to a quantity of the property to be measured.

Absorption spectrophotometries direct a particular wavelength of light through a sample and determine the amount of light absorbed by the sample. There are also turbidimetric techniques that rely on the development of precipitate within a sample. The amount of precipitate is directly related to the desired property within the sample to be measured. Again, a light source is passed through the sample and measurements of loss of light are taken. The measurement of absorbed or blocked light is related to the concentration of measured property.

Figure 11:
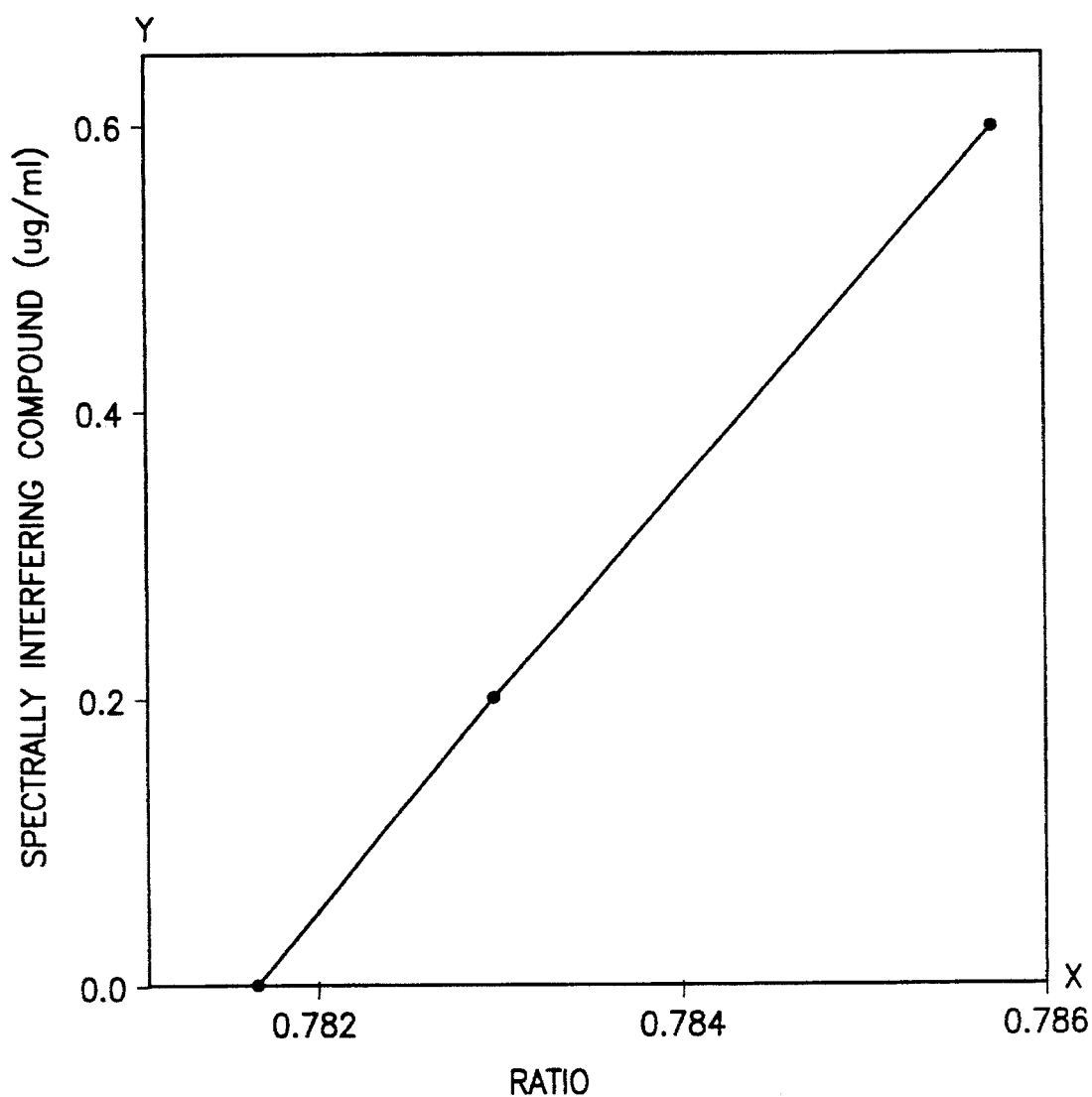
FIG. 11 is a plot of an application of the invention to determine the concentration of colored component in a sample.

The present invention improves upon the sensitivity of the turbidimetric or calorimetrical assay by the following method: to a turbidimetric or calorimetrical test setup that includes both standards (knowns) and samples (unknowns) exactly as according to specification except comprising 10 to 50 fold less property to be measured. The standard method is developed as specified and then an equal amount of fluorescent label is added to each sample and standard. The samples are placed in a fluorimeter and the entire emission spectra are scanned. A ratio of low energy to high energy region of each spectrum is determined as in line D or line H of table 2. Instead of determination of the efficiency of fluorescence the concentration of each standard is used as the Y axis coordinate. The plot is shown in FIG. 11. The unknown sample ratios are applied to the X axis and the concentration of desired component is determined according to the concentrations of the standards by the spectral interference resulting from the developed color or turbidity in response to the desired component. This is an improvement upon the conventional technique of using absorption or optical density because of the two types of instruments, the fluorimeter and spectrophotometer, the fluorimeter in general is far more sensitive.

Having thus described the invention with particular reference to the preferred forms thereof, it will be obvious that various changes and modifications may be made therein without departing from the spirit and the scope of the invention as defined by the appended claims.

Wherefore I claim:

1. A method for determining a corrected fluorescent value representative of activity within a fluorescent assay in the presence of an unknown test sample comprising the steps of:

(a) placing said assay in a fluorimeter and exciting a fluorescent label of said assay with light energy at its excitation wavelength;

(b) selecting and examining a plurality of emission wavelengths within the emission spectrum of said fluorescent label to obtain an intensity value at a wavelength of the emission maximum of said fluorescent label and intensity values at other wavelengths within the emission spectrum;

(c) developing a ratio between the intensity values at said selected wavelengths of lower energy with the intensity values of said selected wavelengths within the emission spectrum;

(d) adding a specified amount of a spectrally interfering component to said assay and examining the intensity values of said fluorescent label at said selected wavelengths to obtain an efficiency standard of said fluorescent label in the presence of a spectrally interfering component;

(e) applying said ratio to said efficiency standard to establish a correction factor of said fluorescent label; and (f) determining a corrected fluorescence value of said assay at its emission maximum by dividing the intensity at said emission maximum by said correction factor, whereby said corrected fluorescence value is representative of an activity within said assay when said unknown test sample is present therein.

2. The method of claim 1, wherein said activity is a protein activity and said test sample is a plant extract.

3. The method of claim 1, wherein said activity is a bonding characteristic of a protein to a receptor.

4. The method of claim 1, wherein said activity is a bonding characteristic of a protein to a protein.

* * * * *